US009416838B2

(12) United States Patent  
Garrish

(10) Patent No.: US 9,416,838 B2  
(45) Date of Patent: Aug. 16, 2016

(54) HYDRAULIC TENSION SPRING

(71) Applicant: Spring Loaded Technology Incorporated, Halifax (CA)

(72) Inventor: Robert Garrish, Halifax (CA)

(73) Assignee: Spring Loaded Technology Incorporated, Halifax (CA)

( * ) Notice: Subject to any disclaimer, the term of this patent is extended or adjusted under 35 U.S.C. 154(b) by 238 days.

(21) Appl. No.: 14/317,447

(22) Filed: Jun. 27, 2014

(65) Prior Publication Data

US 2015/0377313 A1 Dec. 31, 2015

(51) Int. Cl.
*F16F 5/00* (2006.01)
*A61F 5/01* (2006.01)
*F16F 9/16* (2006.01)

(52) U.S. Cl.
CPC ... *F16F 5/00* (2013.01); *A61F 5/01* (2013.01); *F16F 9/16* (2013.01)

(58) Field of Classification Search
CPC ........... A61F 2/38; A61F 2/64; A61F 5/0123; A61F 5/0125; A61F 2005/0134; A61F 2005/0179
USPC .................. 601/33; 602/5, 12, 14, 16, 23, 26; 267/34, 66, 70, 73, 287, 289
See application file for complete search history.

(56) References Cited

U.S. PATENT DOCUMENTS

| | | | | |
|---|---|---|---|---|
| 3,799,159 A * | 3/1974 | Scott | ......................... | A61F 2/64 602/16 |
| 5,395,304 A * | 3/1995 | Tarr | ...................... | A61F 5/0125 602/16 |
| 5,472,410 A * | 12/1995 | Hamersly | ............. | A61F 5/0125 601/33 |
| 5,683,353 A * | 11/1997 | Hamersly | ............. | A61F 5/0125 601/33 |
| 6,001,075 A * | 12/1999 | Clemens | ............... | A61F 5/0123 602/16 |
| 6,746,248 B2 * | 6/2004 | Eastwood | ............. | A61F 5/0102 434/253 |
| 8,317,874 B2 * | 11/2012 | Pusch | ....................... | A61F 2/60 602/16 |
| 2007/0010772 A1 * | 1/2007 | Ryan | ..................... | A61F 5/0123 602/26 |
| 2013/0325123 A1 * | 12/2013 | Clifford | .................... | A61F 2/38 623/13.12 |
| 2015/0119777 A1 * | 4/2015 | Garrish | ................. | A61F 5/0123 602/16 |

* cited by examiner

*Primary Examiner* — Christopher Schwartz

(74) *Attorney, Agent, or Firm* — Walker & Jocke

(57) ABSTRACT

A hydraulic tension spring comprises a block comprising at least one liquid-impermeable cylinder and at least one piston disposed through an open end of the cylinder. The piston provides a piston guide within a liquid containment space within the cylinder filled with hydraulic fluid. A tensioning member moves the piston or the cylinder relative to the other to compress the hydraulic fluid and load the spring, while the piston guide keeps the piston axially aligned to prevent buckling.

20 Claims, 6 Drawing Sheets

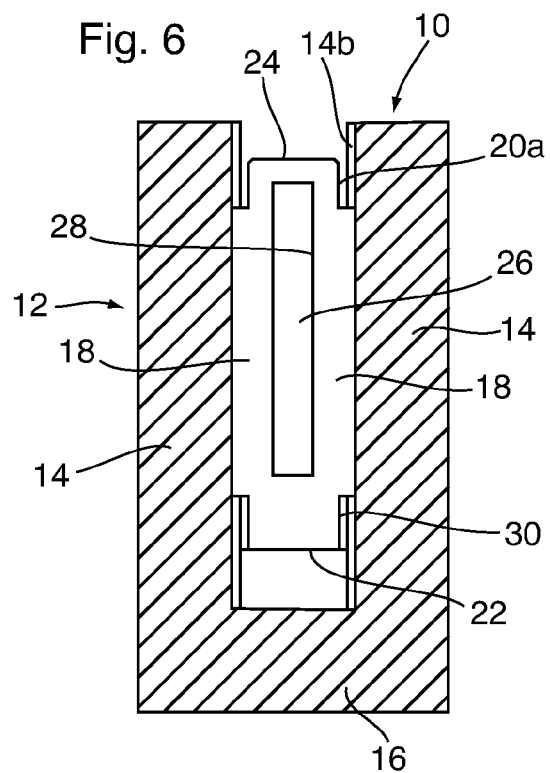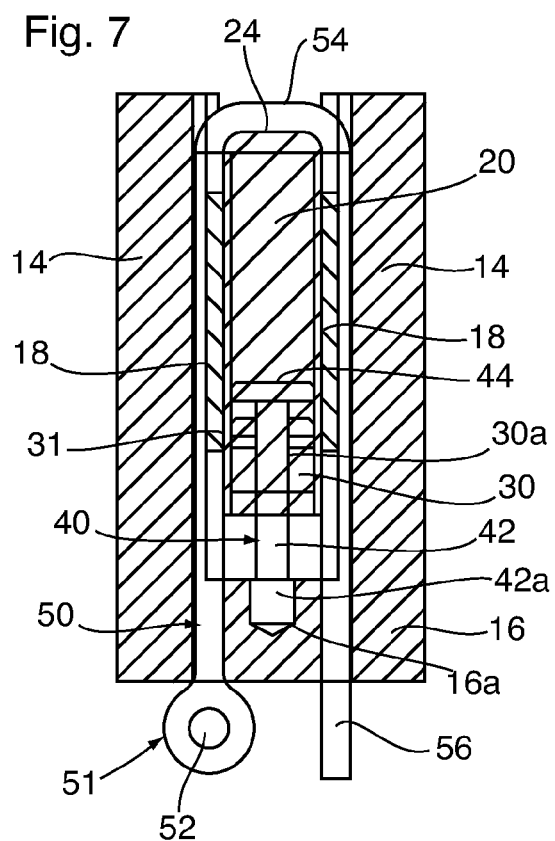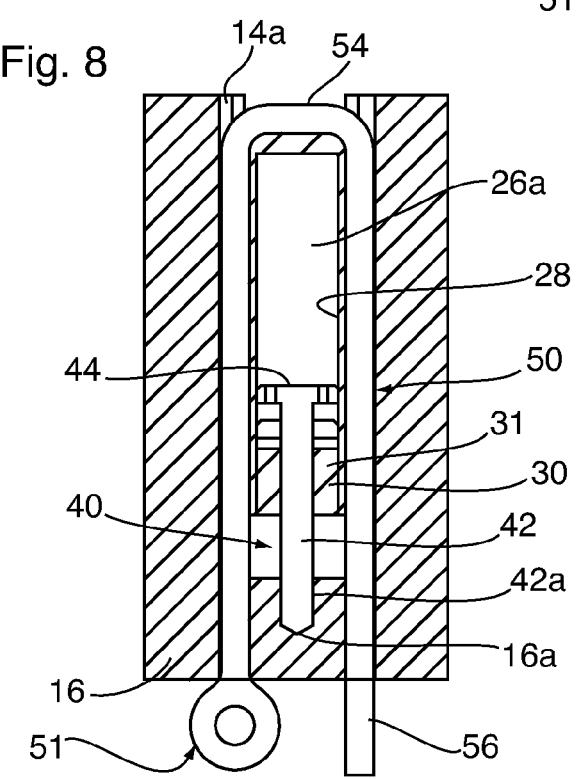

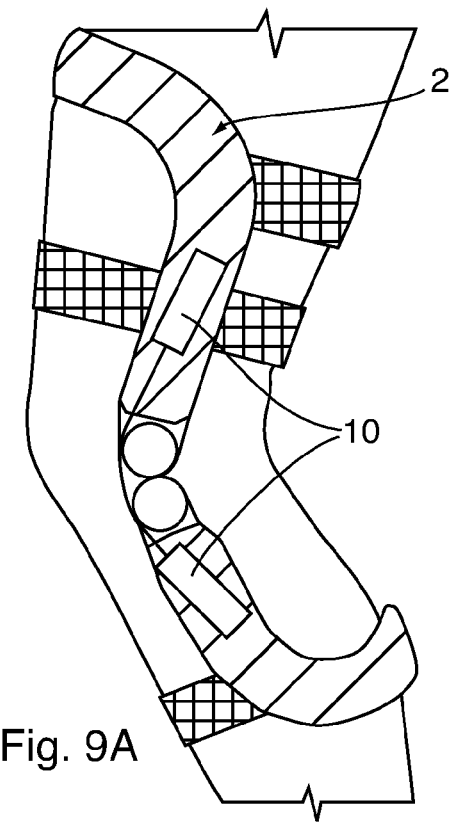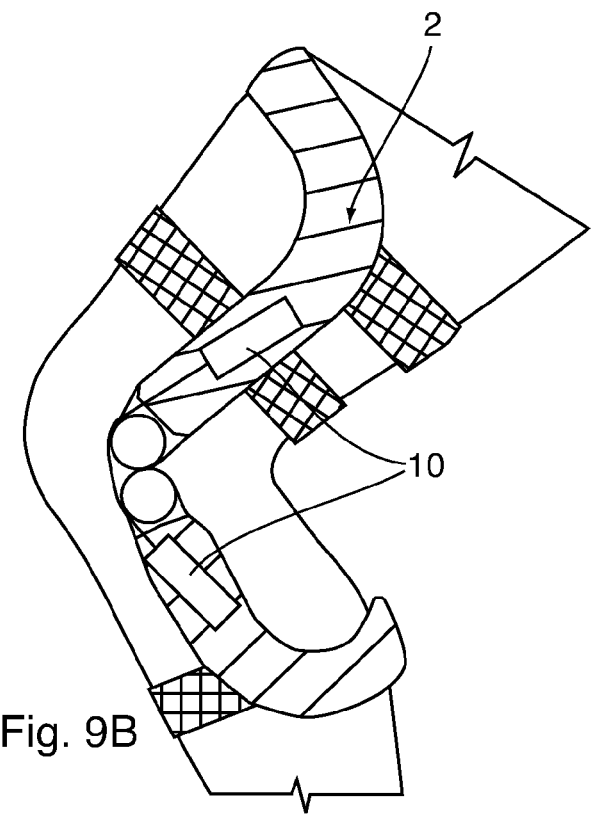
Fig. 9A  Fig. 9B
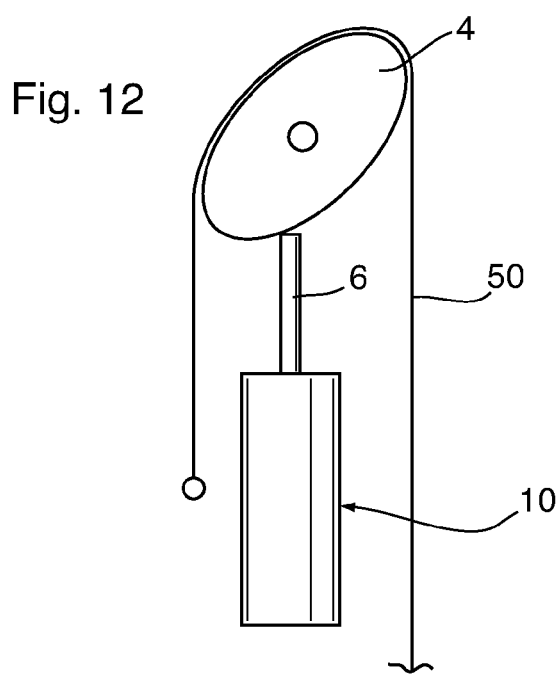
Fig. 12

HYDRAULIC TENSION SPRING

FIELD OF THE INVENTION

This invention relates to springs. In particular, this invention relates to a hydraulic tension spring.

BACKGROUND OF THE INVENTION

Springs are used in myriad applications and environments. Different kinds of springs have different loading characteristics, including different force curves, elastic deformation limits and plastic deformation limits. Certain applications have strict loading requirements over the operative range of the spring, and accordingly require a spring with fairly precise tolerances under light and heavy loads.

For example, a knee brace can be designed to provide an assistive force that helps the user to extend their knee. Many individuals suffer from knee problems, often due to a prior knee injury. Some such problems can significantly affect mobility and/or the ability to support the injured person. While corrective measures such as exercise and physiotherapy, or in more serious cases surgery, can assist in correcting or partially alleviating some knee problems, there remains a need in many cases for knee support and extension augmentation.

Particularly where there has been ligament damage, for example a tear or strain in the anterior cruciate ligament (ACL), medial collateral ligament (MCL) or lateral collateral ligament (LCL), a knee brace can be used to both provide support and enhance extension strength, and thus reduce the load on the injured knee. Conventional knee braces that provide active assistance to knee extension are designed to yield when the knee is flexed, loading a torsion spring or compression spring in the process. The spring is loaded when the user bends their leg, and when extending their leg the spring unloads applying a force that augments the extension action. This also helps to support the user and prevent collapse if the injured knee buckles.

However, conventional springs do not provide sufficient force to significantly enhance knee extension or resist buckling of the knee. Additionally, a brace for a limb can be designed to provide a specific force profile or 'force curve' over the range of motion of the user's limb, and it is important to maintain a consistent force curve over the thousands of cycles that such a brace is likely to be used, which can be difficult to achieve using conventional springs.

Hydraulic compression springs, commonly known as "liquid die springs", are known for use in the tool and die industry. In a liquid die spring a piston compresses a liquid to load the spring, and the potential energy of the spring is released when the compressive force is removed from the piston.

Liquid die springs have a very low compression ratio and a smooth force curve, making them well suited for short-stroke, highly linear applications such as tool and die machinery. However, a significantly longer stroke is required for applications such as knee braces, and this is problematic given the forces Forcing the piston into the spring can be equivalent to applying up to a 1500 lb end load on a 0.125" steel rod that is more than an inch long. The piston will buckle unless it is very carefully guided, which can damage or destroy the piston, the seal, or both.

BRIEF DESCRIPTION OF THE DRAWINGS

In drawings which illustrate by way of example only preferred embodiments of the invention.

FIG. 6 is a front cross-sectional elevation of the spring of FIG. 1 taken along the line 6-6 in FIG. 2.

FIG. 7 is a front cross-sectional elevation of the spring of FIG. 6 taken along the line 7-7.

FIG. 8 is a front cross-sectional elevation of the spring of FIG. 6 taken along the line 8-8.

FIG. 9A is a schematic elevation showing the spring of FIG. 1 fixed to a knee brace in the rest position.

FIG. 9B is a schematic elevation showing the spring of FIG. 1 fixed to a knee brace in the loaded condition.

FIG. 12 is a schematic elevation showing an alternate tensioning mechanism for the spring 10, interposing an eccentric element 4 to provide a non-linear force curve.

DETAILED DESCRIPTION OF THE INVENTION

Figure 1:
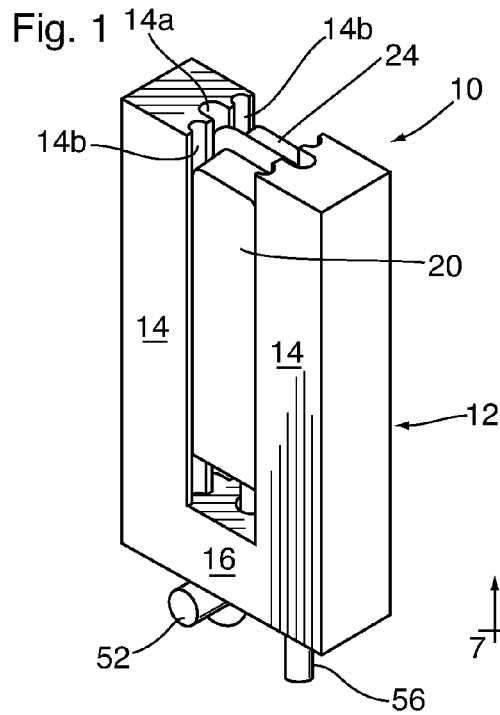
FIG. 1 is a perspective view of a first embodiment of a hydraulic tension spring according to the invention.

The invention will be described in the environment of a knee brace 2. It will be appreciated that the hydraulic tension spring of the invention can advantageously be used in many other applications and the principles of the invention will apply equally. It will also be appreciated that all the advantages of the invention do not necessarily apply to every embodiment.

An embodiment of a hydraulic tension spring 10 according to the invention is illustrated in FIGS. 1-5. The spring 10 comprises a block 12 comprising opposed guide legs 14 maintained in fixed spaced apart relation by a base 16. Opposed interior faces of the legs 14 each provide a cord guideway 14a for receiving a cord 50, as described below, and in the preferred embodiment comprise one or more guide channels 14b. The frame 12 is preferably molded from hardened steel, or another strong, rigid material that resists substantial flexing under the maximum forces ordinarily encountered in the environment in which the spring 10 is used, for example a knee brace 2 as shown in FIGS. 9A and 9B.

Figure 2:
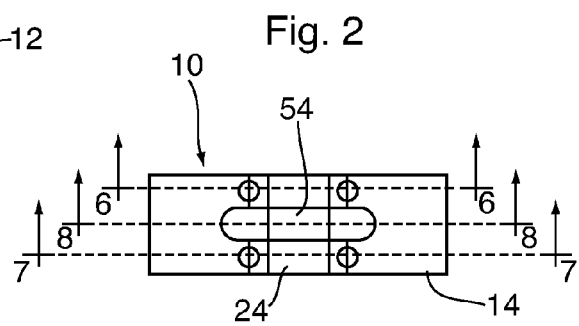
FIG. 2 is a top plan view of the spring of FIG. 1.
Figure 3:
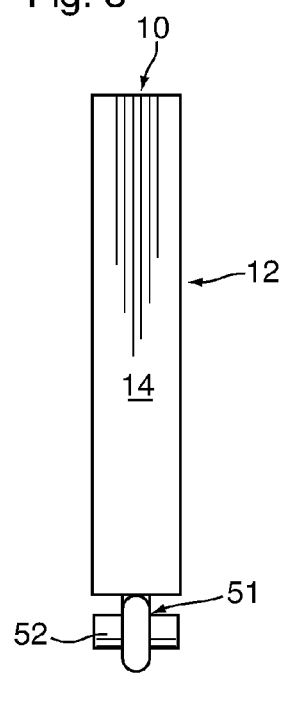
FIG. 3 is a side elevation of the spring of FIG. 1.
Figure 4:
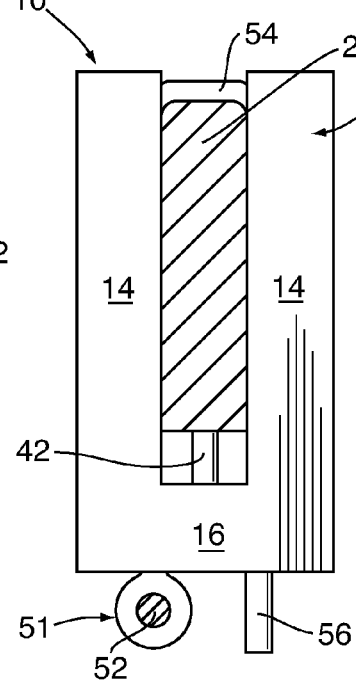
FIG. 4 is a front elevation of the spring of FIG. 1, with the cylinder in the rest position.
Figure 5:
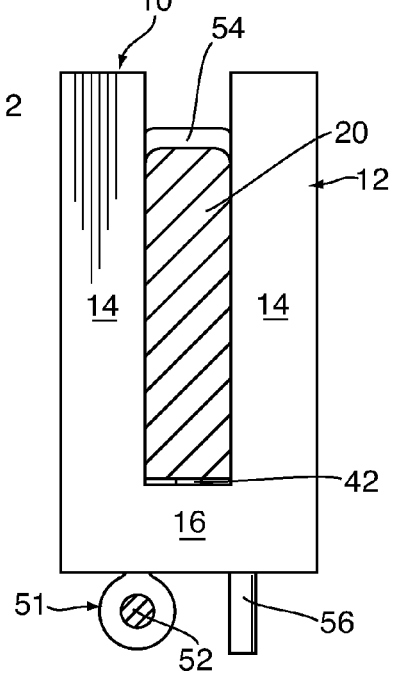
FIG. 5 is a front elevation of the spring of FIG. 1, with the cylinder in the loaded position.

The spring 10 further comprises a moving cylinder 20 having an open end 22 and a closed end 24. The cylinder 20 is preferably molded from hardened steel or another strong, rigid material and has a wall thickness which resists substantial flexing under the maximum forces ordinarily encountered in the environment in which the spring 10 is used. The cylinder 20 is mounted in the frame 12, and constrained to axial movement along the guide legs 14, in the preferred embodiment by a series of ball bearings 18 nesting in the guide channels 14b and complementary guide channels 20a formed along the longitudinal sides of the cylinder 20. The guide channels 14b, 20a are accordingly semi-circular in cross-section in the embodiment illustrated, complementing the size and shape of the ball bearings 18 when the cylinder 20 is mounted in the frame 12, as best seen in FIG. 2. The cylinder 20 is thus able to move between a rest position, shown in FIG. 4A, and a loaded position, shown in FIG. 4B.

The cylinder 20 comprises a liquid-impermeable cavity 26 defining a liquid containment space that is filled with a hydraulic fluid, for example a silicone-based liquid or other suitable hydraulic fluid having the desired compressibility characteristics. The closed end 24 of the cylinder 20 is preferably formed integrally with the cavity wall 28. A bushing 30, for example composed of hardened steel or another suitably durable material, capable of being formed to high-precision tolerances and withstanding the high pressures (e.g. up to 6,000 lbs. of force), is preferably threadedly engaged within the other end 22 of the cylinder 20 and retains a hydraulic seal 31 formed form polyethylene, Teflon or another suitable material, seen in FIG. 8, seated within the cylinder 20, to contain the hydraulic fluid.

A piston 40 is disposed through the bushing 30 and seal 31 into the cavity, the piston rod 42 slidably extending through a central axial opening 30a through the bushing 30 and seal 31 (seen in FIG. 8). One end of the piston rod 42 provides a foot 42a bearing against the frame 12, for example embedded in a recess 16a in the base 16. The other end of the piston 40 provides a piston guide 44 which is liquid-permeable and closely fitted to the cavity wall 28, to maintain the piston 40 in precise axial alignment during each stroke. Thus, when the cylinder 20 is in the rest position shown in FIG. 4 the liquid is in a substantially uncompressed condition.

The spring 10 further comprises a flexible, inelastic cord 50 for applying a loading force to the spring 10. The cord 50 may for example be composed of a polyethylene fibre, for example Honeywell Spectra™ high-strength light-weight polyethylene fibre, which has a very high tensile strength and a very low elasticity. The cord 50 extends through the frame 12, for example through an opening 16b through the base 16, and has an anchored end 51 restrained against movement into the frame 12, for example via enlargement 52 which is too large to traverse the opening 16b. As will be evident from the operation of the invention, described below, while it is necessary to restrain the anchored end 52 of the cord 50 from being pulled into the frame 12 when the cord 50 is tensioned, specifically where the anchored end 52 is anchored is a matter of choice depending upon the environment in which the spring 10 is used. It is possible to fix the anchored end 51 to any suitable structure, including a movable structure or another spring 10, as long as the cord 50 can be tensioned at the desired point to load the spring 10.

The cord 50 in the embodiment shown is thus anchored against the base 16 via anchored portion 51 and extends through the opening 16b. The cord 50 continues through the cord guideway 14a axially along one side 18 of the cylinder 20 (on the left in the orientation shown in the drawings). A tensioning portion 54 is disposed around the closed end 24 of the cylinder 20 and runs down the other cord guideway 14a (on the right in the orientation shown in the drawings) along the side of the cylinder 20. A free portion 56 of the cord is movable into and out of the frame 12, for example extending through opening 16c in the base 16.

The cord 50 thus wraps around the cylinder as shown, such that the cylinder 20 is in the rest position when the cord 50 is not being tensioned. It will be appreciated that the cord 50 could enter and exit the frame 12 at intermediate positions along the legs 14, and does not need to wrap completely around the sides and closed end 24 of the cylinder, but the embodiment illustrated is advantageous for obtaining the maximum leverage against the compressive resistance of the spring 10 during loading.

In operation, the frame 12 is fixed to a stable structure, for example the upper portion of the hinged knee brace 2 shown in FIGS. 9A and 9B, and the free end 56 of the cord 50 is fixed to a structure that moves in relation to the fixed frame, for example fixed to the lower portion of the hinged knee brace 2, either directly or fixed to another spring 10 which is in turn fixed to the lower portion of the hinged knee brace 2 as shown in FIGS. 9A and 9B. As the free portion 56 of the cord 50 is tensioned, for example when a user flexes their knee, the cylinder 20 is forced toward the base 16 of the frame 12 as shown in FIG. 4B, in relative terms causing the piston rod 42 to move further into the cylinder 20. The displacement of hydraulic fluid caused by the greater volume of piston rod 42 intruding into the cylinder compressing the hydraulic fluid in the cylinder 20 and loads the spring 10. As the tension on the cord 50 is reduced, for example when a user extends their knee, the hydraulic fluid decompresses, moving the cylinder 20 toward the rest position and releasing the potential energy in the spring 10 into the cord 50, assisting the extension motion.

FIGS. 7 and 8 illustrate cross-sectional views of the above-described embodiment of the invention respectively taken along the lines 7-7 and 8-8 in FIG. 2.

Conventional liquid die springs have no space constraints relative to stroke length, and as such can use much thicker cylinders in comparison with their force output. Because some of the environments in which tension springs of the invention can be advantageously used require that the spring 10 be compact, for example in a knee brace 2 where there is limited room for a spring and weight is a factor, in a spring 10 according to the invention the stroke length can approach the length of the cylinder 20 itself, which is nearly one-half of the total height of the frame 12 in the embodiments illustrated. This requires a very small cylinder, with attendant reduction in the wall thickness of the cylinder and therefore reduced resistance to buckling. In order to prevent buckling, the piston 40 is precision-guided by the piston guide 44 to remain oriented axially with a very high precision throughout the entire stroke length. It is also advantageous in a spring 10 according to the invention to utilize a very thin bushing 30 in order to reduce the overall length of the frame 12, since the bushing thickness is added to the required height of the cylinder assembly.

Figure 10:
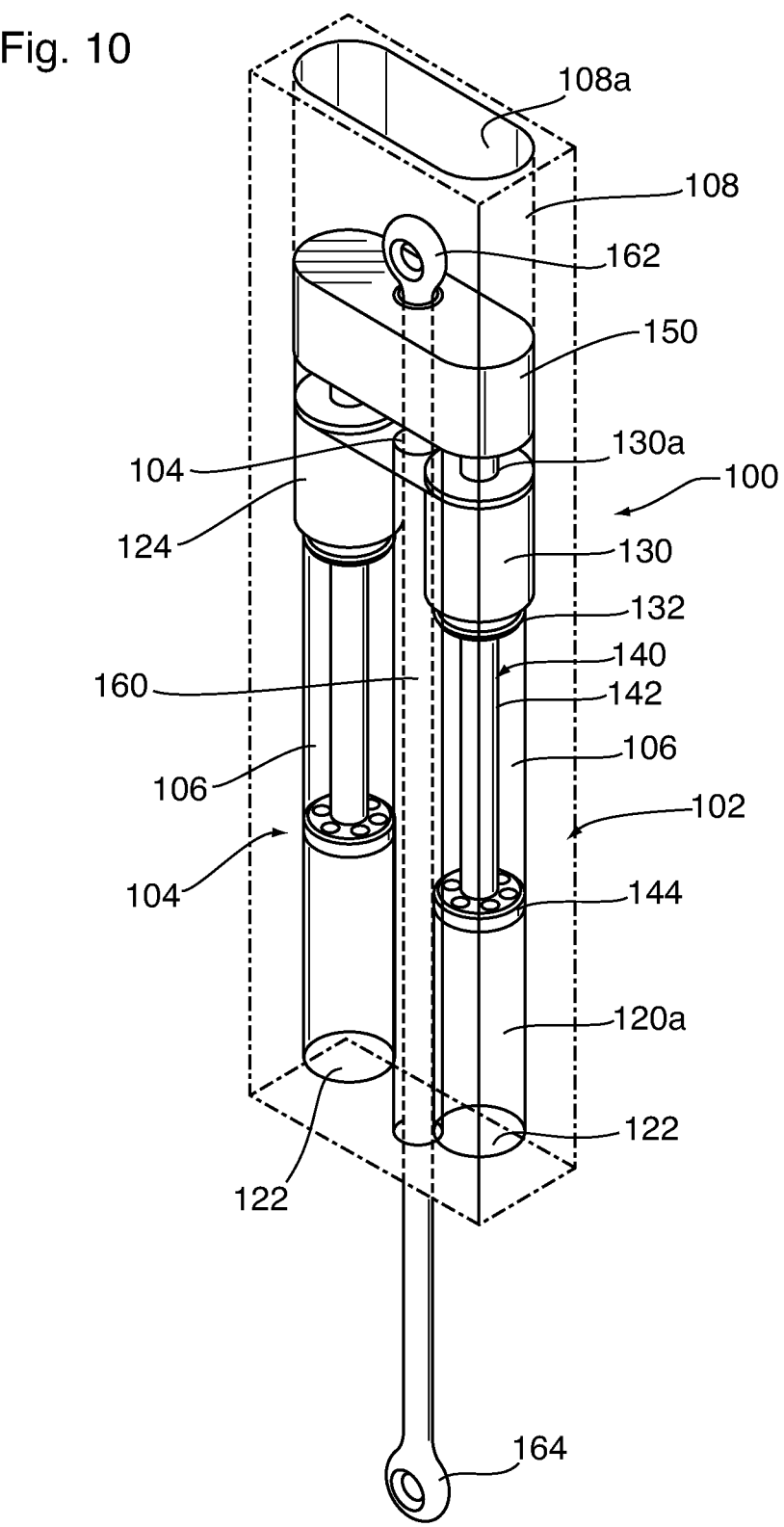
FIG. 10 is a perspective view of a further embodiment of a hydraulic tension spring according to the invention having multiple cylinders.

FIG. 10 illustrates a further embodiment of a hydraulic tension spring 100 according to the invention comprising multiple stationary cylinders with moving pistons. In this embodiment a pair of cylinders 120 are fixed within a block 102 and pistons 140 are movable to extend into and retract from the cylinders 120.

The block 102 thus comprises a cylinder portion 104 comprising a pair of cylinders 120 disposed longitudinally along the block 102 in parallel relation, in communication with a piston rod cap guide portion 108 containing a piston rod cap 150. The block 102 is preferably molded from hardened steel, or another strong, rigid material that resists substantial flexing under the maximum forces ordinarily encountered in the environment in which the spring 10 is used, for example a knee brace 2.

The cylinders 120 each have a closed end 122 and an open end 124. Each cylinder 120 is defined by a liquid-impermeable wall having a thickness which resists deformation under the maximum forces ordinarily encountered in the environment in which the spring 10 is used. The closed end 122 of each cylinder 120 is preferably formed as an integral part of the block 102.

Figure 11A:
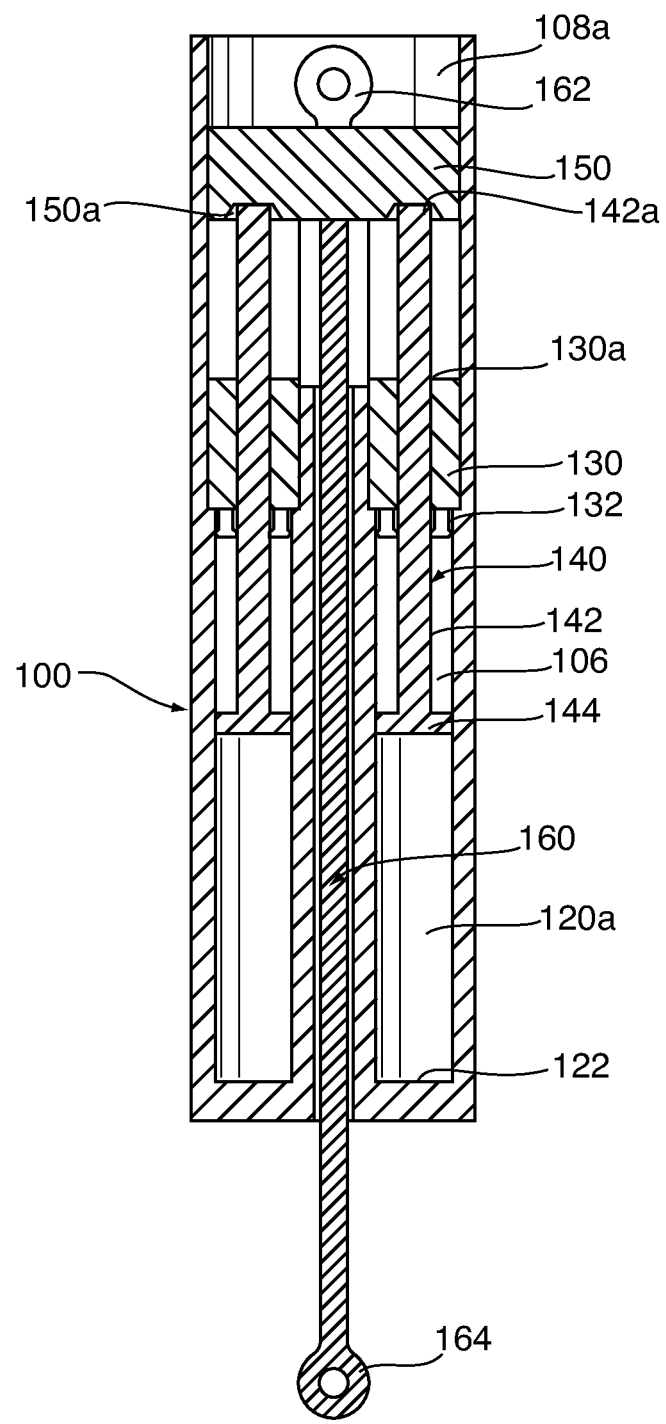
FIG. 11A is an elevational cross-section of the spring of FIG. 10 showing the spring in a rest condition.

In this embodiment a piston 140 comprises a piston rod 142 slidably disposed through a seal retainer cap 130, for example composed of hardened steel or another suitably durable material capable of being formed to high-precision tolerances, disposed in the open end 124 of each cylinder 120. The seal retainer cap 130 may for example have a threaded exterior engaged to interior threading about the end of the cylinder 120. The piston rod 142 slidably extends from the cap guide portion 108 of the block 102 into the cylinder 120 through a central axial opening 130a through the seal retainer cap 130 and through hydraulic seal 132. The hydraulic seal 132 defines a liquid containment space 120a within the cylinder 120 that is filled with a liquid, for example a silicone-based liquid or other suitable hydraulic fluid having the desired compressibility characteristics. Thus, when the piston 140 is in the rest position shown in FIG. 11A the liquid entirely fills the liquid containment space 120a, and is in a substantially uncompressed condition.

Figure 11B:
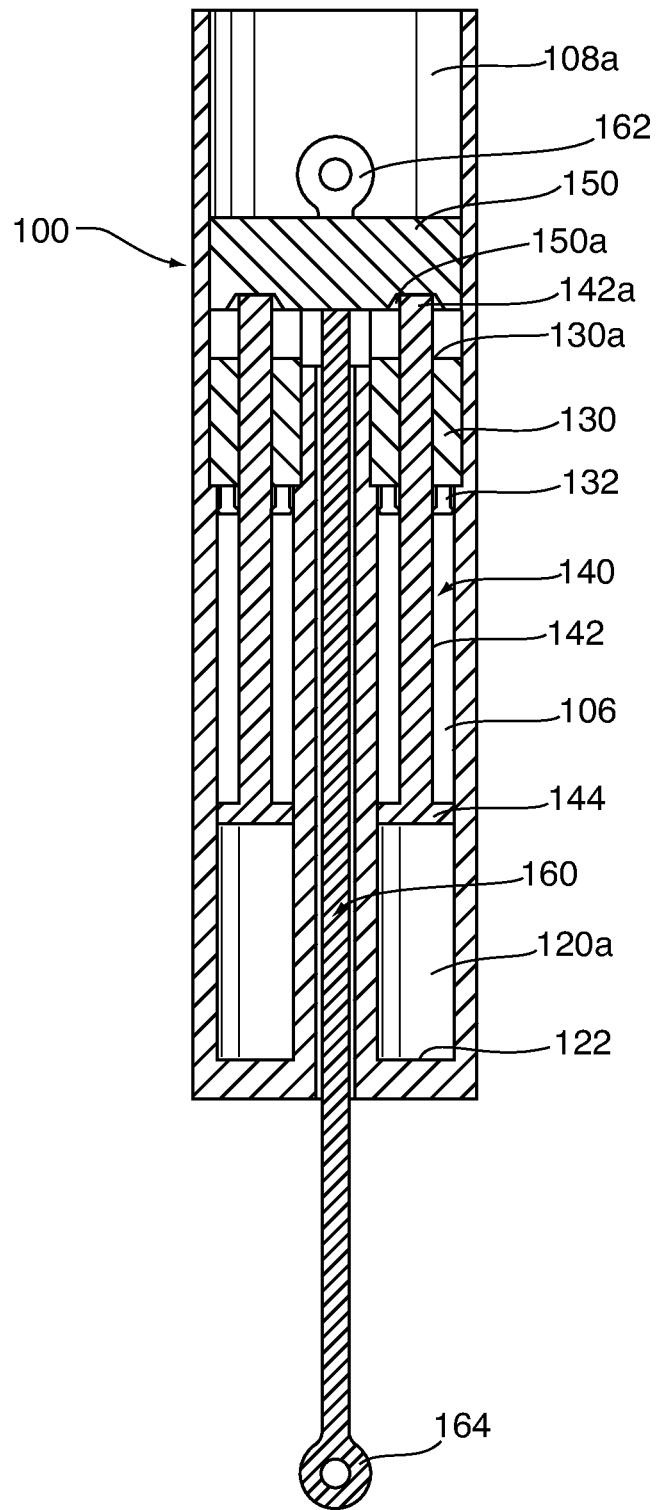
FIG. 11B is an elevational cross-section of the spring of FIG. 10 showing the spring in a tensioned condition.

In this embodiment the end of the piston rod 142 within the cylinder 120 is provided with a piston guide 144, which is liquid-permeable and thus moves freely through the liquid containment space 120a while retaining the piston rod 132 in precise axial alignment within the block 102. The opposite end of each piston rod 142 provides a foot 142a (seen in FIGS. 11A and 11B) against which the piston rod cap 150 bears, for example by lodging the ends of each piston rod 142 in a recess 150a to maintain the piston rods in position symmetrically about the centre of the piston rod cap 150 so that substantially equal force is applied to each piston rod 142. The piston rod cap 150 is constrained to axial movement relative to the cylinders 120 by the wall 108a of the cap guide portion 108 of the block 102.

A tensioning member, for example a tensioning rod 160, extends through a bore 152 disposed axially through the piston rod cap 150 at a position between the two piston rods 142, and extends through a bore 104 disposed axially between the two cylinders 120. An enlarged terminus 162 of the tensioning rod 160 prevents the tensioning rod 160 from slipping out of the bore 152 in the piston rod cap 150, essentially affixing the tensioning rod 160 to the piston rod cap 150, and the other end of the tensioning rod is accessible from outside the block 102 and preferably provides a connector, for example a loop 164, for affixing a cord or other flexible or rigid inelastic tensioning element (not shown).

In the operation of this embodiment, the block 102 is fixed in position, for example affixed to the cuff of a knee brace, and a tensioning element (not shown) is affixed to the connector 154 with the spring 100 in the rest position shown in FIG. 10A. As tension is applied to the tensioning element and transmitted to the tensioning rod 160, the enlargement 162 draws the piston rod cap 150 toward the cylinders 140. The piston rod cap 150 in turn forces the pistons 140 into the cylinders 120, to the tensioned position shown in FIG. 10B. The increasing volume of piston rod 142 within the liquid containment space 120a as the piston rod 142 enters the cylinder 108 displaces the hydraulic fluid, compressing the hydraulic fluid in the liquid containment space 120a and loading the spring 100. When the tension is released from the tensioning rod 160, the spring 100 releases, forcing the piston 140 to return to the rest position of FIG. 10A and in the process imparting the stored potential energy to the load.

It will be appreciated that in the multiple-cylinder embodiment, additional cylinders 120 may be provided as long as all cylinders 120 are distributed symmetrically about an axis containing the tensioning rod 160. In this fashion tension applied to the tensioning rod 160 is distributed equally amongst the cylinders, ensuring that the tensioning force is applied axially to each piston 140 so as to avoid buckling.

It will also be appreciated that the piston guide 144 is preferably shaped to be complementary to the cross-section of the cylinder 120, for example circular in the embodiment illustrated, for maximum lateral stability. However, the piston guide 144 need only contact the wall of the cylinder 120 at a sufficient number of points to maintain the axial orientation of the piston 140, as shown centred within the cylinder 120, for example at three points spaced circumferentially equally about the cylinder 120.

FIG. 12 illustrates an embodiment in which the spring 10 is mounted adjacent to an eccentric element, for example cam 4 which is rotatably mounted to the structure to which the spring 10 is fixed (e.g. a knee brace 2). As tension is applied to the cord 50, the cam 4 rotates, applying a force to the plunger 6 which increases as the cam is rotated. The plunger 6 ion turn transfers this force to the spring (e.g. bearing against the outer face 24 of the cylinder 20 shown in FIGS. 1-8).

Various embodiments of the present invention having been thus described in detail by way of example, it will be apparent to those skilled in the art that variations and modifications may be made without departing from the invention. The invention includes all such variations and modifications as fall within the scope of the appended claims.

The invention claimed is:

1. A hydraulic tension spring, comprising
at least one cylinder having a sealed portion defining a liquid containment space,
for each of the at least one cylinders,
   a piston comprising a piston rod, the piston rod comprising
      a compressing portion having a smaller diameter than the cylinder and extending axially through a hydraulic seal into the liquid containment space, and
      an external portion accessible from outside the liquid containment space,
   one of the cylinder and the piston being fixed relative to a frame and the other of the cylinder and the piston being movable axially relative to the frame,
   a guide for maintaining the movable one of the cylinder and the piston oriented axially relative to the frame, and
a tensioning member bearing against the movable one of the at least one cylinder and the piston, for compressing the at least one cylinder relative to the piston,
whereby when the frame is fixed in place and tension is applied to the tensioning member, the compressing portion of the piston rod intrudes further into the liquid containment space, compressing the hydraulic fluid and loading the spring.

2. The hydraulic tension spring of claim 1 wherein the cylinder is stationary relative to the frame and the compressing portion of the piston rod is provided with a fluid-permeable piston guide movable along the cylinder and maintaining compressing portion of the piston rod spaced from a wall of the cylinder to thereby retain the axial orientation of the piston.

3. The hydraulic tension spring of claim 2 wherein applying a tensioning force to the tensioning member draws a piston rod cap against the piston, the piston rod cap being positioned so as to apply force axially to the external portion of the piston rod.

4. The hydraulic tension spring of claim 3 wherein the external portion of the piston rod is seated in a recess in the piston rod cap.

5. The hydraulic tension spring of claim 3 comprising a plurality of cylinders and pistons, wherein the piston rod cap is positioned so as to apply force axially to the external portions of each of the piston rods and the tensioning member applies force to the piston rods centrally between the cylinders so as to apply the axial force equally to the external portion of each piston rod.

6. The hydraulic tension spring of claim 5 wherein the tensioning member is movably disposed through the frame centrally between the cylinders.

7. The hydraulic tension spring of claim 5 wherein the piston rod cap is slidably disposed in a piston rod cap guide portion disposed adjacent to sealed ends of the cylinders.

8. The hydraulic tension spring of claim 2 wherein the piston rod guide comprises a member having a shape complementary to a cross-section of the cylinder and mounted substantially radially to the compressing portion of the piston rod.

9. The hydraulic tension spring of claim 8 wherein the piston rod guide is perforated.

10. The hydraulic tension spring of claim 2 wherein the frame comprises a block containing the at least one cylinder.

11. The hydraulic tension spring of claim 1 wherein the piston is fixed relative to the frame and the cylinder moves along a guide formed by the frame.

12. The hydraulic tension spring of claim 11 wherein the guide comprises opposed guide legs maintained in fixed spaced apart relation by a base.

13. The hydraulic tension spring of claim 12 wherein ball bearings are disposed in tracks provided along the legs and abutting the cylinder.

14. The hydraulic tension spring of claim 12 wherein the tensioning member comprises a substantially inelastic cord extending over the cylinder, whereby applying a tensioning force to the cord draws the cylinder toward the base to cause the compressing portion of the piston rod to intrude further into the liquid containment space.

15. The hydraulic tension spring of claim 14 wherein the cord extends through the base.

16. The hydraulic tension spring of claim 15 wherein the cord extends through a track along the legs of the frame and around the cylinder such that both ends of the cord extend through the base, providing leverage whereby the force applied to the cylinder is greater than the tensioning force applied to the cord.

17. The hydraulic tension spring of claim 12 wherein the external portion of the at least one piston rod is seated in a recess in the base of the frame.

18. The hydraulic tension spring of claim 1 wherein a cam is interposed between the tensioning member and the piston, whereby a substantially linear force applied to the tensioning member applies a non-linear force to the piston.

19. The hydraulic tension spring of claim 18 wherein the cam is disposed on a cam wheel abutting the piston and rotated by applying force to the tensioning member.

20. The hydraulic tension spring of claim 1 affixed to a limb brace having upper and lower portions, wherein the spring is affixed to one of the upper and lower portions and the tensioning member is affixed, directly or indirectly, to the other of the upper and lower portions.

\* \* \* \* \*